(12) United States Patent
Cheng et al.

(10) Patent No.: US 6,500,972 B2
(45) Date of Patent: Dec. 31, 2002

(54) SYNTHESIS OF TMBQ WITH TRANSITION METAL-CONTAINING MOLECULAR SIEVE AS CATALYSTS

(75) Inventors: Soofin Cheng, Taipei; Chia-Lung Tsai; Berryinne Chou, both of Kaohsiung; Debasish Das, Taipei, all of (TW)

(73) Assignee: Chinese Petroleim Corp. (TW)

( * ) Notice: Subject to any disclaimer, the term of this patent is extended or adjusted under 35 U.S.C. 154(b) by 0 days.

(21) Appl. No.: 09/912,841

(22) Filed: Jul. 25, 2001

(65) Prior Publication Data

US 2002/0143198 A1 Oct. 3, 2002

(51) Int. Cl.⁷ .................. C07C 50/04; C07C 45/29; C07C 45/36
(52) U.S. Cl. .................. 552/296; 552/310; 568/342; 568/346; 568/358
(58) Field of Search .................. 552/296, 310; 568/342, 346, 358

(56) References Cited

U.S. PATENT DOCUMENTS 5,175,318 A * 12/1992 Minisci et al.
6,262,311 B1 * 7/2001 Maassen et al.

OTHER PUBLICATIONS

Mahalingam et al. "A Convenient Synthesis of Alkyl Substituted p–Bezoquinones from Phenols and H2O2 over TiAPO–5 Molecular Sieve Catalyst". Chem. Letters. (1999) (6) p. 455–456.*

Chai–Lung Tsai et al., Synthesis of TMBQ Using Cu(I-I)–Substituted MCM–41 As The Catalyst; Applied Catalysis A: Genreal 208 (Feb. 2001), pp. 279–289.

* cited by examiner

Primary Examiner—Johann Richter
Assistant Examiner—Sikarl A. Witherspoon
(74) Attorney, Agent, or Firm—Powell Goldstein Frazer & Murphy LLP

(57) ABSTRACT

A method of oxidizing trimethylphenol (TMP) to trimethylbenzoquinone (TMBQ) by various molecular sieves containing various transition metals. In this method, TMP, a molecular sieve containing a transition metal in its framework, an oxidant and a solvent are mixed together to form a reaction system. The reaction system reacting at a temperature of about room temperature to 150° C. to obtain TMBQ, and the concentration of TMP is about 5–60% wt.

22 Claims, No Drawings

SYNTHESIS OF TMBQ WITH TRANSITION METAL-CONTAINING MOLECULAR SIEVE AS CATALYSTS

CROSS-REFERENCE TO RELATED APPLICATION

This application claims the priority benefit of Taiwan application serial no. 090100156, filed Jan. 3, 2001, the full disclosure of which is incorporated herein by reference.

BACKGROUND OF THE INVENTION

1. Field of Invention

The present invention relates to a synthetic method of molecular sieves containing transition metals. More particularly, the present invention relates to a synthetic method of a mesoporous molecular sieve containing Cu and Al in its framework.

The present invention also relates to a method of oxidizing trimethylphenol (TMP) to trimethylbenzoquinone (TMBQ) by using molecular sieves, which comprise the molecular sieve containing Cu and Al in its framework, as catalysts.

2. Description of Related Art

Recently, the global market of Vitamin E has dramatically increased. The main markets are in medical ingredients and nutrition foods. Since the starting material, i.e. 2,3,6-trimethyl-1,4-hydroquinone (TMHQ), is not easily obtained in bulk, the price of Vitamin E is quite high. Therefore, researchers have widely studied how to efficiently manufacture TMHQ at a lower cost.

In the past two decades, many chemical processes have been developed to manufacture TMHQ by using TMP as the starting material. Sumitomo Chemical Company uses chlorine gas to chlorinate TMP, then nitric acid is used to oxidize TMP to TMHQ (U.S. Pat. No. 3,932,475). The advantage of this process is that the price of TMP is quite cheap, but one problem is that it produces a lot of pollutants. More than 50 kg of pollutive effluent is produced for every kilogram of TMHQ. [C. Mercier and P. Chabardes, in M. G. Scaros and M. Prunier (Eds.), Catalysis of Organic Reactions, Marcel Decker, New York, 1994, pp. 213–221 ].

TMP is oxidized to TMBQ, and then TMBQ is hydrogenated to TMHQ by other patents. Catalysts, which can be used in the oxidation step, include $MnO_2$ and saturated organic acids (U.S. Pat. No. 3,927,045), inorganic or organic acids of Tl (III) (U.S. Pat. No. 3,910,967), chelating complexes of Co (U.S. Pat. No. 4,250,335), complexes of Fe or Mn (U.S. Pat. No. 5,712,416), cupric oxide or cuprous oxide (U.S. Pat. No. 4,491,545), and aqueous solutions (U.S. Pat. No. 4,828,762) or saturated alcohol solutions (U.S. Pat. No. 5,041,572) of cuprous halide/alkaline metal halide. Generally used catalysts in the hydrogenation step include platinum or palladium supported on zeolites or aluminum oxide, and hydrogen gas is used to hydrogenate TMBQ to TMHQ (U.S. Pat. No. 4,491,545 and U.S. Pat. No. 4,828,762).

Some papers about oxidizing TMP to TMBQ are published, such as Ito et al. (S. Ito, K. Aihara, M. Matsumoto, Tetrahedron Lett., 1983, 24, 5249), have used many kinds of metal oxides and metal salts as catalysts, acetic acid and 30% hydrogen peroxide solution are respectively used as a solvent and an oxidant. They found that the best reaction result was obtained when $RuCl_3$ was used as the catalyst. The yield of TMBQ was up to 90%. Since $RuCl_3$ is readily soluble in the reaction solution, $RuCl_3$ is hardly separated from the solution to be reusable. Furthermore, the cost of $RuCl_3$ is quite high, and thus this method is not economic.

Japanese Shimizu et al. (M. Shimizu, H. Orita, T. Hagakawa, K. Takehira, Tetrahedron Lett., 1989, 30, 471) and Russian Kholdeeva et al. (O. A. Kholdeeva, A. V. Golovin, R. I. Maksimovskaya, I. V. Kozhenikov, J. Mol. Catal., 1992, 75, 235) respectively use hetero-polyacids and acetic acid to be the catalyst and the solvent. When 60% wt. $H_2O_2$ is used as the oxidant, the yield of TMBQ is the highest (about 80%). However, the consumption of $H_2O_2$ is very large, and the hetero-polyacids are too readily soluble in water to be isolated from the reaction solution to be reused again.

Dutchman Jansen et al. used hetero-polyacids adsorbed on active carbons as catalyst (J. J. Jansen, H. M. van Neldhuizen, H. van Bekkum, J. Mol. Catal. A, 1996, 107, 241), therefore he hoped to increase the easiness of separating the catalyst from the reaction solution. However, washout of hetero-polyacids adsorbed on active carbons is still occurring, thus the practicability is not high.

The turn over number (TON) of catalysts used in the above references is at most about 4–10. Most oxidation catalysts mentioned above are soluble in organic solvents or water; therefore solvents are needed for recycling these oxidation catalysts to extract them from the reaction mixtures. This extraction procedure makes the whole reaction process more complicated and it still has a large space to improve.

The widest used molecular sieve is the zeolite, of which pore size is in the microporous range, i.e. about 0.5–1 nm. Therefore, it's only application was in catalyzing chemical reactions of small molecules. However, the development of mesoporous molecular sieves, of which pore size is about 2–10 nm, has made them applicable in catalyzing chemical reaction of larger molecules, especially in cracking heavy oil and production of drugs and fine chemicals. When transition metal is added in the molecular sieve, the reaction types that can be catalyzed by the molecular sieve have expanded from acid catalyzed reaction to redox reaction.

In the last ten years, molecular sieves containing transition metal have been popular to be used in synthesis of TMBQ in order to resolve the problem of recovering catalysts from homogeneous reaction systems. For example, liquid reaction system using zeolites containing Ti or V as catalysts and aqueous solution of $H_2O_2$ as oxidant can effectively oxidize phenol to hydroquinone and catechol (J. S. Reddy, S. Sivasanker and P. Ratnasamy, J. Mol. Catal., 1992, 71, 373 and A. V. Ramaswany, S. Sivasanker and P. Ratnasamy, Micro. Mater., 1994, 2 , 451). Molecular sieves containing copper ions are used in decomposing NO, and those molecular sieves containing $Cu^{2+}$ are prepared by ion-exchange between cations of molecular sieves and $Cu^{2+}$.

SUMMARY OF THE INVENTION

The invention provides a method of oxidizing trimethylphenol (TMP) to trimethylbenzoquinone (TMBQ).

In this method, TMP, a molecular sieve containing a transition metal in its framework, an oxidant and a solvent are mixed to form a reaction system, and the reaction system reacts at a suitable temperature to obtain TMBQ. The concentration of the TMP is about 5–60% wt. The reaction temperature is about room temperature to about 150° C., the preferred reaction temperature is about 40–80° C., and the more preferred temperature is about 50–60° C.

The molecular sieve that can be used in this invention comprises a zeolite, a mesoporous molecular sieve of hexagonal or cubic lattice structure, and an aluminophosphate molecular sieve. The transition metal described above can be Ti, V, Cr, Mn, Fe, Co, Ni, Cu, Zn, Nb, Mo, Ru and W, and the amount of the transitioin metal is about 0.1–10% wt. of the molecular sieve.

The zeolite described above can be ZSM-5, ZSM-11, Zeolite-Y, Zeolite-X, Zeolite-A or β-zeolite. The mesoporous molecular sieve described above comprises MCM-41 and MCM-48, and the preferred ones are MCM-41 containing V or Cu/Al. The aluminophosphate molecular sieve described above comprises $AlPO_4$-5, $AlPO_4$-8, $AlPO_4$-11, $AlPO_4$-31, SAPO-37 and VPI-5, and the preferred ones are $AlPO_{4-5}$ containing Ti, Co or Cu.

The oxidant's concentration described above is about 5–60% wt., and it comprises $H_2O_2$ or ROOH such as t-BuOOH. If oxygen gas is used as oxidant, the $O_2$ flows into the reaction system at a flow rate of 1–20 mL/min.

The solvent's concentration described above is about 5–60% wt., and it can be nitrites such as $CH_3CN$; alcohols such as methanol, ethanol, propanol and butanol; aldehydes such as $CH_3CHO$ and PhCHO; and carboxylic acids such as acetic acid.

This invention also provides a method of forming a mesoporous molecular sieve containing Cu and Al in the framework.

In this method, a Si-containing compound, a Cu-containing compound, a Al-containing compound, a template reagent and a solvent are mixed together to obtain a mixing solution. In the mixture solution, the Al/Si molar ratio is between about 0–0.2, the Cu/Si molar ratio is between about 0–0.1, and the template reagent/Si molar ratio is between about 0.1–2.

The Si-containing compound can be an inorganic silicate such as water glass (sodium silicate), or an organic Si-containing compound such as tetraethoxysilicate (TEOS). The Cu-containing compound can be an inorganic copper salt such as $Cu(NO_3)_2$. The Al-containing compound can be an inorganic aluminate such as sodium aluminate, or an organic Al-containing compound such as triethoxyaluminate or tripropoxyaluminate.

The template reagent can be a tetraethyl ammonium salt, a tetrapropyl ammonium salt, a long-chain-alkyl-trimethyl ammonium salt, a copolymer or combinations thereof. The carbon number of the long-chain-alkyl-trimethyl ammonium salt is 12–20. The solvent can be water, methanol, ethanol, propanol, butanol or combinations thereof. The only requirement for mixing various solvents is that these solvents can form a single-phase system.

The pH of the mixture solution is adjusted to about 9–11 when the mixing solution's pH is larger than 11, or the mixture solution's pH is adjusted to about 0.1–3 when the solution's pH is 3–9. The adusting pH step can be accomplished by adding acids such as common used HCl, $HNO_3$ or $H_2SO_4$.

The mixture solution undergoes a hydrothermal reaction under a temperature of about 80–200° C. for about 1–10 days to form the mesoporous molecular sieves. Precipitate is separated from the products of the hydrothermal reaction, and then it is washed and dried. The precipitate is calcined at a temperature of about 500–800° C. to remove the template reagent in the mesoporous molecular sieve's pores.

It is to be understood that both the foregoing general description and the following detailed description are by example only, and are intended to provide further explanation of the invention as claimed.

DESCRIPTION OF THE PREFERRED EMBODIMENTS

I. Method of Synthesizing Molecular Sieves Containing Transition Metals

This invention provides a method of synthesizing an aluminosilicate molecular sieve containing transition metals. The synthesis steps are as follow:

1. Both the silicon-containing compound and the aluminum-containing compound or the solutions of both compounds are mixed together, wherein the Al/Si molar ration is 0 to 0.5. The silicon-containing compound can be, for example, an inorganic silicate or an organic Si-containing compound, and the aluminum-containing compound can be, for example, an inorganic aluminate or an organic Al-containing compound.

2. An organic template reagent and a salt of transition metal (M) or solutions thereof are added to the reaction solution of step 1, and the M/Si molar ratio is 0 to 0.5. The organic template can be, for example, a tetraethyl ammonium salt, a tetrapropyl ammonium salt, a long-chain-alkyl-trimethyl ammonium salt or other surfactants, wherein the carbon number of the long-chain-alkyl-trimethyl ammonium salt's long-chain-alkyl group is preferred to be 12 to 20 and more preferred to be 16.

3. A hydrothermal reaction is performed for the resulting solution of step 2 under a temperature of 80–200° C.

4. Precipitate is separated from the resulting solution of step 3. The precipitate is washed with water and is then dried.

5. The precipitate is calcined under a temperature of about 500–800° C. to remove the organic template in the pores of the aluminosilicate molecular sieve.

This invention also provides another method of synthesizing an aluminophosphate molecular sieve. The synthesis steps are as follows:

1. Both the phosphorous-containing compound and the aluminum-containing compound or the solutions of both compounds are mixed together, wherein the Al/P molar ration is 0.5 to 1.5. The phosphorous-containing compound can be, for example, an inorganic phosphate or an organic P-containing compound, and the aluminum-containing compound can be, for example, an inorganic aluminate or an organic Al-containing compound.

2. A salt of transition metal (M) or a solution thereof are added to the reaction solution of step 1, and M/Al molar ratio is about 0 to 0.5.

3. An organic template reagent is added to the resulting solution of step 2. The organic template can be, for example, dipropyl amine, triethyl amine or tripropyl amine, wherein the preferred organic template is triethyl amine.

4. A hydrothermal reaction is performed for the resulting solution of step 3 under a temperature of about 100–250° C.

5. Precipitate is separated from the resulting solution of step 4. The precipitate is washed with water and is then dried.

6. The precipitate is calcined under a temperature of about 500–800° C. to remove the organic template in the aluminophosphate molecular sieve's pores.

Several kinds of molecular sieves containing transition metals are synthesized by methods mentioned above. These molecular sieves comprise ZSM-5 (a microporous aluminosilicate zeolite), AlPO$_4$-5 (a microporous aluminophosphate molecular sieve), and mesoporous MCM-41. Many molecular sieves containing transition metals are found to have catalytic activity for oxidizing TMP to TMBQ, especially the MCM-41 containing V or Cu/Al. Therefore, MCM-41 containing V or Cu/Al will be the main examples for discussion described below.

1. Synthesis Method of MCM-41 Containing Cu/Al

A Si-containing compound, an Al-containing compound, a Cu-containing compound, a template reagent and a solvent are mixed together to form a mixture solution, wherein 0<Al/Si molar ratio≦0.2, 0<Cu/Si molar ratio≦0.1, and 0.1≦template/Si molar ratio≦2. The Si-containing compound can be, for example, an inorganic silicate such as water glass, i.e. sodium silicate, or an organic Si-containing compound such as tetraethoxysilicate (TEOS). The Al-containing compound can be, for example, an inorganic aluminate such as sodium aluminate or an organic Al-containing compound such as triethoxyaluminate or tripropoxyaluminate. The Cu-containing compound can be, for example, an inorganic copper salt such as Cu(NO$_3$)$_2$. The template reagent can be, for example, a tetraethyl ammonium salt, a tetrapropyl ammonium salt, a long-chain-alkyl-trimethyl ammonium salt, copolymer or combinations thereof. The preferred carbon number of the long-chain-alkyl-trimethyl ammonium salt's longest alkyl chain is 12 to 20. The solvent can be, for example, water, methanol, ethanol, propanol, butanol or combinations thereof, if the different solvents can be mixed to form a single-phase system.

If pH value of the mixture solution is larger than 11, for example, when water glass is used as the Si source, the pH of the mixture solution is adjusted to about 9–11. If pH value of the mixture solution is between 3 to 9, for example, when TEOS is used as the Si source, the pH of the mixture solution is adjusted to about 0.1–3. The pH adjustment can use acids such as commonly used HCl, HNO$_3$ or H$_2$SO$_4$.

The mixture solution undergoes a hydrothermal reaction at a temperature of about 80–200° C. for 1–10 days. Precipitate (i.e. MCM-41 molecular sieve) is then separated from the mixture solution, washed with water and dried. Finally, the precipitate is calcined at a preferred temperature of about 500–800° C. to remove the template reagent in the pores of MCM-41. A real synthetic example will be given as follows.

4.25 g of cetyltrimethylammonium bromide (CTMABr) is dissolved in 30 g of water to get a template solution. An appropriate amount of Cu(NO$_3$)$_2$ is added to 100 mL of water, then the mixture is stirred to get a Cu(NO$_3$)$_2$ solution. An appropriate amount of NaAlO$_2$ is added to 15 g of water, then the mixture is stirred for 5 min; 5.33 g of water glass and 15 g of water are then added to get a mixed solution of sodium aluminate and sodium silicate. The Cu(NO$_3$)$_2$ solution is added to the mixed solution of sodium aluminate and sodium silicate, the template solution is then added after stirring for 10 min. After stirring for 5 min, the pH of the resulting solution is adjusted to 9.5 to 10. After 2 days of stirring, the solution undergoes the hydrothermal reaction at a temperature of about 100° C. for 7 days. Next, after the solution's temperature is lowered to room temperature, the solution is filtered to get the final powder product. The powder is washed with a large amount of water then it is put into an oven to dry at a temperature of about 50° C. Finally, the powder is calcined at a temperature of about 560° C. for 12 hours to get MCM-41 containing Cu/Al in its framework.

2. Characterization of MCM-41 Containing Cu/Al

In the X-ray powder diffraction (XRD) spectrum of MCM-41 as synthesized, diffraction peaks at 4.08, 2.37, 2.06 and 1.57 nm of d-spacing appear, which individually represent the Miller index (100), (110), (200) and (210) diffraction planes of hexagonal crystal structure. After high-temperature calcining to remove CTMABr in the pores of MCM-41, diffraction peaks in XRD spectrum move toward lower d-spacing direction, which is accompanied by the occurrence that the full-line-width at half-maximum (FWHM) of diffraction peaks is decreased and the intensity of diffraction peaks is increased. This XRD spectrum change indicates that the structure of MCM-41 is condensed after calcination, and therefore the pore size is decreased but the crystal structure is improving.

For the MCM-41 with the same Al content but different Cu content, the XRD spectra's diffraction peaks do not show large changes, but the FWHM has increased as the Cu content of MCM-41 has increased. For the MCM-41 with the same Cu content but different Al content, the FWHM of the XRD spectra's diffraction peak becomes broader when the Al content is greater than 3%. When the Al content is greater than 10%, the crystal structure is poor and the diffraction peaks move to lower d-spacing positions.

The XRD spectra's changes show that when Cu and/or Al content is greater than a certain amount, the framework of MCM-41 is twisted. Therefore, Cu and Al should mostly enter the framework of MCM-41, and the pores are hexagonally arranged. The MCM-41 as synthesized can maintain the hexagonal-arranged pore structure after calcination at the temperature of 560° C.

Inductive Coupled Plasma-Atomic Emission Spectroscopy (ICP-AES) is used to detect the relative amount of various elements in samples, which are listed in Table 1. The number before "C" in the sample name represent the atomic ratio (%) of Cu/Si, and the number before "A" in the sample name represent the atomic ratio (%) of Al/Si. The Cu/Si ratio of MCM-41 products is usually lower than that of the initial reaction solutions, which shows that Cu is not entirely incorporated into the framework of MCM-41. As for the sample OC2A, the Al/Si ratio is higher than that of the initial reaction solution. It may be that a portion of skeletal SiO$_2$ is solubilized in aqueous solution, which makes the Al content relatively increase. It is indicated that Al can more easily replace skeletal Si than Cu.

TABLE 1

| ICP-AES analysis results of MCM-41 containing Cu/Al. | | | | |
|---|---|---|---|---|
| Sample name | Atomic Ratio of Cu/Si (%) | | Atomic Ratio of Al/Si (%) | |
| of MCM-41 | Reactant | Product | Reactant | Product |
| 0C0A | 0 | 0 | 0 | 0 |
| 0C2A | 0 | 0 | 2 | 2.16 |
| 1C2A | 1 | 0.83 | 2 | 1.35 |
| 2C0A | 2 | 1.65 | 0 | 0 |
| 2C2A | 2 | 1.74 | 2 | 1.71 |

II. Oxidation Reaction of TMP Catalyzed by a Molecular Sieve in a Liquid-phase Reaction System This invention provides a method of oxidizing TMP to produce TMBQ, which is catalyzed by a molecular sieve. This method comprises a reaction system, which includes TMP, a molecular sieve containing a transition metal in its framework, an oxidant, and a solvent those are mixed together to undergo a reaction under a suitable temperature to obtain TMBQ. The concentration of TMP is about 5–60% wt. The preferred reaction temperature is about room temperature to about 150° C., and the more preferred reaction temperature is about 40° C. to 80° C.

The molecular sieve containing a transition metal in their framework can be, for example, a zeolite, a mesoporous molecular sieve of hexagonal or cubic crystal structure and an aluminophosphate molecular sieve. The transition metal contained in the framework of the molecular sieve can be, for example, Ti, V, Cr, Mn, Fe, Co, Ni,. Cu, Zn, Nb, Mo, Ru or W, and the content of the transition metal in the framework of the molecular sieve is about 0.1–10% wt. The zeolite can be, for example, ZSM-5, ZSM-11, Zeolite-Y, Zeolite-X, Zeolite-A or β-Zeolite. The mesoporous molecular sieve can be, for example, MCM-41 (hexagonal crystal structure) or MCM-48 (cubic crystal structure). The aluminophosphate molecular sieve can be, for example, $AlPO_4$-5, $AlPO_4$-8, $AlPO_4$-11, $AlPO_4$-31, SAPO-37 or VPI-5 and $AlPO_4$-5, and those are better to contain Ti, Co or Cu in their framework.

The oxidant's concentration is preferred to be about 5–60% wt. and the oxidant can be, for example, $H_2O_2$ or alkyl peroxide such as tert-butylhydroperoxide (t-BuOOH; abbreviated as TBHP). If molecular oxygen is used as the oxidant, it is better to direct about 1–20 mL/min of oxygen into the reaction system.

The concentration of the solvent is better to be about 5–60% wt. The usable solvent can be nitriles such as methanenitrile ($CH_3CN$), alcohols such as methanol, ethanol, propanol or butanol, aldehyde such as ethanal or benzoaldehyde (PhCHO), and carboxylic acids such as acetic acid.

A working example is described as below. In a three-neck bottle, 2 g of a molecular sieve used as a catalyst is added in a solution containing 10 g TMP (the molar ratio of TMP/solvent is 1/5) to form a mixture and is then stirred. The mixture in the three-neck bottle is then refluxed under a temperature of about 30–80° C. Next, an aqueous solution of $H_2O_2$ (35% wt.) is added to the mixture and stirred for a period of time. The amount of $H_2O_2$ added is equal to the equivalent number of the TMP.

Gas Chromatography-Flame Ionization Detector (GC-FID) is used to analyze the products of the reaction described above. A blank test reaction, which doesn't add the molecular sieve, is also preformed to compare the results of the reaction described above.

Embodiment Oxidizing TMP to TMBQ by Sample 2C2A

Using sample 2C2A as catalyst, $CH_3CN$ as solvent, and $H_2O_2$ as oxidant to catalyze the oxidation of TMP to TMBQ at a temperature of 60° C. The amount of sample 2C2A added is 2 g, the amount of TMP added is 10 g, the amount of $CH_3CN$ added is 5 times of molar number of TMP, and the amount of $H_2O_2$ added is equal to the molar equivalent of TMP.

The analysis of the reaction's products is listed in Table 2. From Table 2, conversion of TMP is more than 60% in the initial 20 min. The conversion of TMP is increased as time passes, and the increasing rate of the conversion is getting slower after 30 min. The yield of TMBQ is also increased as time passes and reaches a maximum at 40 min.

TABLE 2

Analysis results of TMP oxidation.

| Reaction Time (min) | Conversion of TMP (%) | TMBQ yield (%) | TMBQ Selectivity (%) |
|---|---|---|---|
| 20 | 63.7 | 46.7 | 73.3 |
| 30 | 79.7 | 50.3 | 63.1 |
| 40 | 80.5 | 57.6 | 71.6 |

Embodiment 2
The Effect of Cu/Al Content to the TMP Oxidation

TABLE 3

The effect of the Cu/Al content to the TMP oxidation

| MCM-41 As catalyst | Conversion of TMP (%) | TMBQ yield (%) | TMBQ Conversion (%) |
|---|---|---|---|
| 0C0A | 1.1 | 0 | 0 |
| 2C0A | 51.7 | 27.8 | 53.8 |
| 2C1A | 60.5 | 40.6 | 67.1 |
| 2C2A | 63.7 | 46.7 | 73.3 |

Using MCM-41 samples listed in Table 1 as the catalyst to catalyze TMP oxidation, the molar ratio of the reaction system of TMP:$H_2O_2$:$CH_3CN$ is 1:1:3, and 2 g of MCM-41 is added. The reaction time is 20 min, and the reaction temperature is 60° C. The analysis of products is listed in Table 3.

From Table 3, when the MCM-41 without Cu and Al (sample 0C0A) is used as the catalyst, only very low conversion of TMP is detected and no TMBQ is produced. But as long as the MCM-41 contains Cu in its framework (sample 2C0A, 2C1A, and 2C2A), the production of TMBQ is observed. It is indicated that the Cu is the reactive center for oxidizing TMP. From Table 3, it is also found that the yield of TMBQ can be increased if MCM-41 contains Al in its framework.

Embodiment 3
The Effect of Various Preparation Methods and Lattice Structures of Cu-containing Molecular Sieves to TMP Oxidation The product analysis of TMP oxidation catalyzed by various preparation methods and lattice structures of Cu-containing molecular sieves are listed in Table 4. In Table 4, samples 2C0A, 2C1A, and 2C2A are the same as those in Table 1, whereas samples 2C0A-imp, 2C1A-imp1, 2C2A-imp1, and 2C2A-imp2 are prepared from sample 0C0A in Table 1. The preparation method comprises immersing the sample 0C0A in an aqueous solution of Cu and/or Al for a period of time such as for 3 hrs, and then distilling the sample under a vacuum. In Table 4, numbers before C of these sample names represent the Cu/Si atomic ratios (%) of each sample, and numbers before A of these sample names represent the Al/Si atomic ratios (%).

Samples 1% Cu-APO-5 and 1% Cu-APO-5 in Table 4 represent that Cu is added in the gel solution for preparing $AlPO_4$-5, and the amounts added are individually 1% and 2% of Cu/Si atomic ratio. Sample Cu($NO_3$)$_{2(aq)}$ means an aqueous solution of Cu($NO_3$)$_2$, and sample $Al_2O_3$ is powder of aluminum oxide.

From Table 4, if MCM-41 containing Cu is prepared by immersion (2C0A-imp), only trace amounts of TMBQ can be obtained. If MCM-41 is immersed in aqueous solution of Cu and Al (sample 2C1A-imp1, 2C2A-imp1, and 2C2A-imp2) to be used as catalyst, the yield of TMBQ can be greatly increased. However, the yield and selectivity of TMBQ catalyzed by sample 2C1A-imp1, 2C2A-imp1, and 2C2A-imp2 are not good as by sample 2C0A, 2C1A, and 2C2A, which are prepared from the gel solution that Cu and Al are initially added therein.

To understand whether the residual sodium ions affect the catalytic activity of MCM-41 or not, the aluminum source is changed from $NaAlO_2$ (samples 2C1A-imp1 and 2C2A-imp1) to $Al_2(SO_4)_3$ (sample 2C2A-imp2). Comparing the reaction results of samples 2C2A-imp1 and 2C2A-imp2, no significant difference between the TMBQ yields is found (22.8 vs. 17.3).

TABLE 4

The effect of various preparing method and lattice structure of Cu-containing molecular sieves to TMP oxidation

| Catalyst | Conversion of TMP (%) | TMBQ Yield (%) | Selectivity (%) |
|---|---|---|---|
| MCM-41 | | | |
| 2C0A | 51.7 | 27.8 | 53.8 |
| 2C1A | 60.5 | 40.6 | 67.1 |
| 2C2A | 63.7 | 46.7 | 73.3 |
| MCM-41 immersed in aqueous solution of 0.01 M $Cu(NO_3)_2$ | | | |
| 2C0A-imp | 53.1 | 4.3 | 8.1 |
| MCM-41 immersed in aqueous solution of 0.01 M $Cu(NO_3)_2$ and $NaAlO_2$ | | | |
| 2C1A-imp1 | 58.7 | 15.2 | 25.9 |
| 2C2A-imp1 | 56.2 | 22.8 | 40.6 |
| MCM-41 immersed in aqueous solution of 0.01 M $Cu(NO_3)_2$ and $Al_2(SO_4)_3$ | | | |
| 2C2A-imp2 | 64.9 | 17.3 | 26.7 |
| $AlPO_4$-5 | | | |
| 1% Cu-APO-5 | 85.2 | 20.4 | 23.9 |
| 2% Cu-APO-5 | 84.8 | 30.4 | 35.8 |
| No molecular sieves added | | | |
| $Cu(NO_3)_2$ (aq) | 64.9 | 5.3 | 8.2 |
| $Al_2O_3$ | 35.1 | 0 | 0 |

The amount of catalyst added is 2 g, and the molar ratio of TMP:$H_2O_2$:$CH_3CN$=1:1:3. The reaction time is 20 min, and the reaction temperature is 60° C.

Since Cu and Al are in the forms of CuO and $Al_2O_3$ attaching on the framework of molecular sieves that are prepared by the immersing method, $Al_2O_3$ and aqueous solution of $Cu(NO_3)_2$ are also used to catalyze the TMP oxidation. However, there is no TMBQ produced in the reaction catalyzed by $Al_2O_3$. If the molar equivalent number of $Cu(NO_3)_2$ used is the same as that of catalyst 2C2A, only a small amount of TMBQ is detected. This result indicates that $Cu^{2+}$ is the active site of TMP oxidation, and $Cu^{2+}$ and $Al^{3+}$ in the molecular sieve's framework have a better catalytic activity. That is, the catalytic activity of samples 2C0A, 2C1A and 2C2A is not from the $Cu^{2+}$ dissolved in the reaction solution.

For the Cu-containing molecular sieves of various lattice structures, TMBQ is also obtained in the reaction catalyzed by $AlPO_4$-5 (samples 1% Cu-APO-5 and 2% Cu-APO-5). However, the selectivity of $AlPO_4$-5 is worse than that of MCM-41.

Embodiment 4

V-containing MCM-41 Catalyzes TMP Oxidation

TABLE 5

V-containing MCM-41 catalyze TMP oxidation

| TMP:oxidant (molar ratio) | Oxidant | Solvent | Conversion of TMP (%) | Selectivity of TMBQ (%) |
|---|---|---|---|---|
| 1:1 | $H_2O_2$ | $CH_3CN$ | 55 | >95 |
| 1:2 | $H_2O_2$ | $CH_3CN$ | 70 | >96 |
| 1:1 | $H_2O_2$ | Acetone | 40 | >97 |
| 1:1 | TBHP | $CH_3CN$ | 50 | >15 |
| 1:2 | TBHP | $CH_3CN$ | 60 | >10 |

The amount of catalyst added is 0.05 g, that of TMP added is 0.7 g, and that of solvent added is 10 g. The reaction time is 6 hrs, and the reaction temperature is 60° C.

From Table 5, when $H_2O_2$ is used as oxidant, a very high selectivity of TMBQ, larger than 95%, can be obtained. For the solvent used in the reaction system, the effect of methanenitrile ($CH_3CN$) is better than acetone. As for the oxidant used in the reaction system, although a good conversion rate can be obtained by using t-BuOOH to replace $H_2O_2$, many by-products are obtained. Besides, when the amount of oxidant added is more, the conversion rate of TMP is higher. However, the selectivity of TMBQ is not affected much by the amount of oxidant added.

Embodiment 5

$AlPO_4$-5 Containing Various Transition Metals Catalyzes TMP Oxidation

TABLE 6

$AlPO_4$-5 containing various transition metals catalyzes TMP oxidation

| Catalyst | Conversion of TMP (%) | TON | TMBQ Yield (%) | Selectivity (%) |
|---|---|---|---|---|
| 1% Ti-APO-5 | 84 | 203 | 78 | 93 |
| 1% V-APO-5 | 30 | 73 | 25 | 83 |
| 1% Cr-APO-5 | 67 | 162 | 58 | 86 |
| 1% Mn-APO-5 | 68 | 165 | 59 | 87 |
| 1% Fe-APO-5 | 61 | 148 | 51 | 84 |
| 1% Co-APO-5 | 73 | 177 | 65 | 92 |
| 1% Ni-APO-5 | 42 | 102 | 34 | 81 |
| 1% Cu-APO-5 | 91 | 220 | 72 | 79 |
| 1% Zn-APO-5 | 39 | 94 | 32 | 82 |

The amount of catalyst added is 2 g, and TMP:$H_2O_2$:$CH_3COOH$=10 g:12 mL:22 g. The reaction time is 3 hrs, and the reaction temperature is 60° C.

The product analysis of $AlPO_4$-5 molecular sieve containing various transition metals catalyzing TMP oxidation is listed in Table 6. The M/Si atomic ratio of transition metal (M) in the $AlPO_4$-5 (Si) is about 1%. The TMP conversions and the TMBQ yields vary with various transition metals, wherein the conversion of TMP catalyzed by 1% Cu-APO-5 is the highest and that by 1% Ti-APO-5 is the second. As for the yield of TMBQ, 1% Ti-AlPO-5 is the highest and 1% Cu-APO-5 the is second. Therefore, the $AlPO_4$-5 molecular sieve containing Cu or Ti in its framework is best for TMP to TMBQ in Table 6.

The number of TMBQ molecules produced by each transition metal, i.e. turn over number (TON), is also shown in Table 6. It is indicated that samples 1% Cu-APO-5 and 1% Ti-APO-5 have high catalytic activity, since the TON of 1% Cu-APO-5 and 1% Ti-APO-5 are more than 200.

Embodiment 6

The Effect of Reaction Temperature to TMP Oxidation Catalyzed by AlPO4-5 Molecular Sieve Containing Cu in its Framework

TABLE 7

The effect of temperature to the TMP oxidation

| Temperature | Conversion | TMBQ | |
| (° C.) | (%) | Yield (%) | Selectivity (%) |
| --- | --- | --- | --- |
| 25 | 0 | 0 | — |
| 40 | 51 | 46 | 92 |
| 50 | 83 | 75 | 90 |
| 60 | 91 | 72 | 79 |
| 70 | 100 | 74 | 74 |
| 95 | 97 | 4.0 | 4.1 |
| 110 | 100 | 1.1 | 0.01 |

The amount of 1% Cu-APO-5 added is 0.2 g. TMP:$H_2O_2$:$CH_3COOH$=1.0 g:1.2 mL:2.2 g. The reaction time is 3 hrs.

In Table 7, the 1% Cu-APO-5 is used as the catalyst and seven reaction temperatures (25, 40, 50, 60, 70, 95 and 100° C.) are used for testing the temperature effect to the TMP oxidation. From Table 7, it is found that TMP oxidation cannot be processed at 25° C. When the temperature reaches 40–50° C., the yield of TMBQ is maintained at about 72–75%, and the selectivity of TMBQ is more than 90%. When the temperature is raised to more than 70° C., the effect is increasing the yields of side products and the selectivity of TMBQ is decreased. As for temperatures above 95° C., a secondary reaction produces side products with larger molecular weight, and the yield and the conversion of TMBQ are further decreased.

Embodiment 7

The Effect of Various Solvents and Various Oxidants to the TMP Oxidation

Sample 2C2A is used as catalyst to explore the effect of various solvents and oxidants. The solvents used have ethanol ($C_2H_5OH$), ethanal ($CH_3CHO$), methanenitrile ($CH_3CN$) and benzoaldehyde (PhCHO), whereas the oxidants used have hydrogen peroxide ($H_2O_2$), TBHP (t-BUOOH), oxygen molecule ($O_2$) The results are listed in Table 8.

In Table 8, when hydrogen peroxide is used as the oxidant and the $C_2H_5OH$ is used as the solvent, the conversion of TMP is very low. When the hydrogen peroxide is used as the oxidant and the $CH_3CHO$ is used as the solvent, the conversion of TMP is much higher but the yield of TMBQ is very low. However, when the $CH_3CN$ and PhCHO is used as the solvent, both the conversion of TMP and the yield of TMBQ are quite high. If TBHP is used as the oxidant, the higher TMP conversion rate and TMBQ yield can be obtained. Therefore, if $H_2O_2$ or TBHP is used as the oxidant, the solvent that is better to use is $CH_3CN$ or PhCHO, and PhCHO is even better. If $CH_3CN$ or PhCHO is used as the solvent, the oxidant that is better to be used is $H_2O_2$ or TBHP, and TBHP is even better.

$O_2$ is also used as oxidant here. The reaction is processed under an $O_2$ flow rate of about 20 mL/min into the reaction system, where the $CH_3CN$ or PhCHO is used as solvent. TMP conversion of about 40% is detected after 2 hrs when PhCHO is used as solvent, and the selectivity of TMBQ is about 52%. As the reaction time increases, the TMP conversion and TMBQ yield are also increased. After 6 hrs, the TMP conversion is up to 82.4%, and the TMBQ yield is also up to 54%. However, when $CH_3CN$ is used as the solvent, no TMBQ is detected after 6 hrs. Therefore, when the $O_2$ is used as the oxidant, PhCHO is better to be used as the solvent.

TABLE 8 the effect of various solvents and oxidants to TMP oxidation

| | | | | | TMBQ | |
| Solvent | Oxidant | Reaction time | Conv. (%) | TON | Yield (%) | Select. (%) |
| --- | --- | --- | --- | --- | --- | --- |
| $C_2H_5OH$ | $H_2O_2$ | 20 min | 2.0 | 2.4 | 0 | 0 |
| $CH_3CHO$ | $H_2O_2$ | 20 min | 68.0 | 82 | 1.3 | 1.9 |
| $CH_3CN$ | $H_2O_2$ | 20 min | 63.7 | 77 | 46.7 | 73.3 |
| $CH_3CN$ | TBHP | 20 min | 97.8 | 118 | 83.2 | 85.1 |
| $CH_3CN$ | $O_2$ | 6 hrs | 17.3 | 21 | 0 | 0 |
| PhCHO | $H_2O_2$ | 20 min | 87.0 | 105 | 68.7 | 78.9 |
| PhCHO | TBHP | 20 min | 98.0 | 118 | 87.5 | 89.3 |
| PhCHO | $O_2$ | 2 hrs | 43.2 | 52 | 22.3 | 51.6 |
| PhCHO | $O_2$ | 4 hrs | 71.4 | 86 | 40.9 | 57.3 |
| PhCHO | $O_2$ | 6 hrs | 82.4 | 96 | 44.6 | 54.1 |

The amount of the catalyst added is 0.2 g. The molar ratio of TMP oxidant ($H_2O_2$ or TBHP): solvent is 1:1:3. The $O_2$ flow is 20 mL/min. The reaction temperature is 60° C.

Embodiment 8

The Catalytic Activity of Regenerate Catalyst

Samples 2C2A (MCM-41) and 1% Cu-APO-5 (AlPO$_4$-5) are used as the catalyst to compare the catalytic activity after catalyst regeneration. The results are listed in Table 9. The method of forming a regenerated catalyst is to separate the catalyst from the reaction solution after the reaction, then the catalyst is washed by a large amount of water. After washing it with water, the catalyst is dried at room temperature and calcined at a temperature of about 560° C. for about 6 hrs.

From Table 9, the regenerated catalyst still has high catalytic activity. The yield and selectivity of TMBQ is almost the same for the catalyst before and after the regeneration. It is shown that the catalyst, i.e. the molecular sieve, can be reused by regenerating process and is very suitable to be used in industry.

TABLE 9

The effect of regenerate catalyst to the TMP oxidation

| | | TMBQ | |
| Catalyst | Conversion (%) | Yield (%) | Selectivity (%) |
| --- | --- | --- | --- |
| 2C2A[a] | 64 | 47 | 73 |
| 2C2A[a] (Regenerate) | 59 | 43 | 72 |
| 1% Cu-APO-5[b] | 91 | 72 | 79 |
| 1% Cu-APO-5[b] (Regenerate) | 76 | 61 | 80 |

[a]The amount of catalyst added is 2 g. The molar ratio of TMP:$H_2O_2$:$CH_3CN$ = 1:1:3. The reaction time is 20 min, and the reaction temperature is 60° C.
[b]The amount of catalyst added is 2 g. TMP:$H_2O_2$:$CH_3COOH$ = 10 g:12 mL:22 g. The reaction time is 3 hrs, and the reaction temperature is 60° C.

From the preferred embodiments described above, various molecular sieves containing various transition metals, especially the MCM-41 containing Cu and Al, can be used as the catalyst to catalyze the oxidation of TMP to TMBQ with a suitable oxidant and under a suitable condition. The TMBQ is the main product of TMP's catalytic oxidation. Therefore, compared with other literatures, this invention has the following advantages:

1. Turn over number of TMBQ by per catalytic active site is higher. The turn over number can be up to 200 by using a suitable oxidant and under a suitable reaction condition. Furthermore, the TMBQ yield can be up to more than 85%.
2. The reaction temperature is lower for the TMP oxidation in this invention. The reaction temperature is about 30–80° C. The reaction time needed is also shorter, only about 6–8 hrs.
3. Many oxidants are applicable. Even if the most inert oxidant, $O_2$, also can be used as the oxidant, wherein the turn over number is about 50. Accordingly, the oxidant can be properly chosen by the price of raw materials. Therefore, the cost and throughput can be selectively adjusted.
4. The raw materials for preparing the catalyst are very cheap and the preparation is very easy. Besides, the molecular sieve catalyst is reusable. Therefore, the impact to the environment can be reduced to the lowest level to fulfill the environmental. protection requirement and economic effect.
5. The molecular sieve catalyst is solid. Therefore, the separation of catalyst from the reaction solution is easy. This makes the catalyst easily reusable, and the purification of TMBQ is also easier to process. As a result, the production cost can be largely reduced.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of preparing trimethylbenzoquinone (TMBQ) from trimethylphenol (TMP) characterized in that the reaction is catalyzed by molecular sieves containing copper and aluminum ions incorporated in the framework with a proper oxidant and a carboxylic-acid-free solvent at a temperature lower than 150° C.

2. The method of claim 1, wherein the molecular sieves comprise aluminophosphate molecular sieves of the crystalline structure selected from the group consisting of $AlPO_4$-5, $AlPO_4$-8, $AlPO_4$-11, $AlPO_4$-31, and VPI-5.

3. The method of claim 1, wherein the molecular sieves comprise zeolites of the crystalline structure selected from the group consisting of ZSM-5, ZSM-11, zeolite-Y, zeolite-X, zeolite-A, and β-zeolite.

4. The method of claim 1, wherein the molecular sieves comprise mesoporous molecular sieves selected from the group consisting of MCM-41, and MCM-48 structures.

5. The method of claim 1, wherein the copper and aluminum contents in the molecular sieves is respectively ranged from 0.1–10% wt and 0.1–45% wt.

6. The method of claim 1, wherein the concentration of the TMP is 5–60% wt.

7. The method of claim 1, wherein the proper oxidant is selected from the group consisting of $H_2O_2$, alkyl peroxide and $O_2$.

8. The method of claim 1, wherein the carboxylic-acid-free solvent comprises nitrites selected from the group consisting of methanenitrile ($CH_3CN$), and benzonitrile.

9. The method of claim 1, wherein the carboxylic-acid-free solvent comprises alcohols selected from the group consisting of methanol, ethanol, propanol, and butanol.

10. The method of claim 1, wherein the carboxylic-acid-free solvent comprises acetone or aldehydes selected from the group consisting of ethanal or benzoaldehyde (PhCHO).

11. The method of claim 1, wherein the temperature is 30–80° C.

12. A method of preparing trimethylbenzoquinone (TMBQ) from trimethylphenol (TMP) characterized in that the reaction is catalyzed by molecular sieves containing vanadium, chromium, manganese, iron or cobalt ions in the framework with a proper oxidant and a carboxylic-acid-free solvent at a temperature lower than 150° C.

13. The method of claim 12, wherein the molecular sieves comprise aluminophosphate molecular sieves of the crystalline structure selected from the group consisting of $AlPO_4$-5, $AlPO_4$-8, $AlPO_4$-11, $AlPO_4$-31, and VPI-5.

14. The method of claim 12, wherein the molecular sieves comprise zeolites of the crystalline structure selected from the group consisting of ZSM-5, ZSM-11, zeolite-Y, zeolite-X, zeolite-A, and β-zeolite.

15. The method of claim 12, wherein the molecular sieves comprise mesoporous molecular sieves selected from the group consisting of MCM-41, and MCM-48 structures.

16. The method of claim 12, wherein the vanadium, chromium, manganese, iron or cobalt contents in the molecular sieves is respectively ranged in 0.1–10% wt.

17. The method of claim 12, wherein the concentration of reactant TMP is ranged in 5–60% wt.

18. The method of claim 12, wherein the proper oxidant is selected from the group consisting of $H_2O_2$, alkyl peroxide and $O_2$.

19. The method of claim 12, wherein the carboxylic-acid-free solvent comprises nitrites selected from the group consisting of methanenitrile ($CH_3CN$), and benzonitrile.

20. The method of claim 12, herein the carboxylic-acid-free solvent comprises alcohols selected from the group consisting of methanol, ethanol, propanol, and butanol.

21. The method of claim 12, wherein the carboxylic-acid-free solvent comprises acetone or aldehydes selected from the group consisting of ethanal or benzoaldehyde (PhCHO).

22. The method of claim 12, wherein the temperature is 30–80° C.

* * * * *